United States Patent [19]

Chess

[11] Patent Number: 5,057,104
[45] Date of Patent: Oct. 15, 1991

[54] METHOD AND APPARATUS FOR TREATING CUTANEOUS VASCULAR LESIONS

[76] Inventor: Cyrus Chess, 49 Blue Spruce Cir., Weston, Conn. 06883

[21] Appl. No.: 358,890

[22] Filed: May 30, 1989

[51] Int. Cl.$^5$ .............................................. A61N 5/06
[52] U.S. Cl. ...................................... 606/9; 128/899; 604/20
[58] Field of Search ............... 128/395, 397, 398, 399, 128/400, 898; 606/9, 10, 13-19; 604/22, 20

[56] References Cited

U.S. PATENT DOCUMENTS

| | | | |
|---|---|---|---|
| 3,307,553 | 3/1967 | Liebener | 128/406 |
| 3,821,510 | 6/1974 | Muncheryan | 128/345 |
| 3,967,627 | 7/1976 | Brown | 128/400 |
| 4,140,130 | 2/1979 | Storm, III | 128/400 |

OTHER PUBLICATIONS

"The Benefit of Chilling in Argon-Laser Treatment of Port-Wine Stains", by Dréno et al; Plastic & Reconstruct, Surg., vol. 75, No. 1, Jan. 1985, pp. 42–45.

Primary Examiner—David Shay
Attorney, Agent, or Firm—Grimes & Battersby

[57] ABSTRACT

A method of treating telangiectasia in a target area in a patient's dermis includes the steps of passing a laser beam against and through the patient's epidermis to the target area and simultaneously subjecting the patients epidermis to a cooling fluid at the location of the epidermis entered by the laser beam. The apparatus for effecting the treatment includes a laser beam source and devices for subjecting the patient's epidermis to a cooling fluid where the laser beam enters the epidermis.

11 Claims, 2 Drawing Sheets

METHOD AND APPARATUS FOR TREATING CUTANEOUS VASCULAR LESIONS

BACKGROUND OF THE INVENTION

I. Field of the Invention

The present invention relates generally to a method and apparatus for treating telangiectasia and, more particularly, to such a method and apparatus in which telangiectasia is treated by simultaneously cooling the site of the telangiectasia while delivering laser light to the site.

II. Description of the Prior Art

Telangiectasia (spider capillaries) of the lower extremities is a condition where previously microscopic blood vessels have become dilated. They are visible through the skin appearing as red, blue or purple variably tortuous lines or patches. The causes of this abnormal enlargement of vessels are not fully understood, and although they are of little medical consequence their cosmetic significance can be great. This is a widespread problem that may cause much concern for those afflicted.

Sclerotherapy is the treatment that is now used. It is considered to be safe, appropriate and relatively effective. Sclerotherapy entails the intravascular injection of one of a variety of agents into the abnormal blood vessels. The substance injected injures the inside of the capillary causing it to shrink or disappear. This treatment is variably painful, approximately 70% effective and usually requires one to two months waiting before improvement can be seen. There can occur, unpredictably, echymotic or hyperpigmented marks as a side effect and these marks may take many months to fade. Scabbing of injection sites, perhaps due to extravasation of the injected sclerosing agent may also occur.

Laser surgery with a variety of different lasers (CO2, Argon, tunable dye) has been utilized in an attempt to find a less painful, more effective treatment. The desire to avoid side effects has also prompted a search for alternative treatment. To date, the ability to improve the outcome by virtue of laser surgery has, unfortunately, not been possible for reasons explained below.

The disadvantages of sclerotherapy, as described above, include the pain of treatment, only partial improvement, and the possibility of long term discoloration that can be more noticeable than the telangiectasia. Although laser surgery (Argon or tunable dye) hurts less than sclerotherapy, it has not offered an improved result. Due to the interaction between laser light and melanin pigments in the epidermis that overlies the target vessels, there can be long term hyperpigmentation, persistent scabs and sometimes permanent scarring.

U.S. Pat. 4,122,853 to Smith, which issued on Oct. 31, 1978, provides an infrared laser photocautery device. There is provided means for delivering a liquid through a passageway for irrigating the area being treated. The fluid is not used for cooling, and the utility of the device is primarily for photo-cauterizing intraocular muscular tissue.

U.S. Pat. 4,381,007 to Doss, which issued on Apr. 26, 1983, relates to a multipolar probe apparatus using radio frequency energy to reshape the cornea of an eye. The surface of the cornea is flushed continuously with a electrically conductive liquid coolant during the operation. No lasers are involved, and the use of the apparatus is limited to reshaping corneas.

U.S. Pat. 4,559,942 to Eisenberg, which issued on Dec. 24, 1985, is a method of using a laser for cataract surgery. The laser passes through a probe to the target tissue and an air cushion is maintained between the probe and the target tissue to prevent physical contact between the radiation outlet of the probe and the target tissue during laser irradiation. At column 4, lines 39–41, it is emphasized that due to air cushion between the probe and the target tissue, the laser radiation passes to the tissue with little loss of heat, thus indicating that it is Eisenberg's intent to conserve, not to dissipate, heat.

U.S. Pat. 4,608,979 to Breidenthal, et al, which issued on Sept. 2, 1986, is directed to nonsurgically fragmenting of kidney stones by an apparatus which produces focused shock waves. A truncated ellipsoidal reflector is positioned against the patient with one focus coincident with the stone. The reflector is filled with a liquid medium having an acoustical impedance similar to living tissue A laser beam is focused at the remaining focus, thereby producing a shock wave which is coupled through the liquid medium and the patients tissue and focused at the stone, to impart a fragmenting stress to the stone. The liquid medium is not used for cooling purposes.

European Patent application No. 073,617 to Pemberg, which has a priority dated of Aug. 25, 1981, provides a laser dental hard piece with a water/air supply tube. There is provided means for pulsating the water alternately with the laser beam if the laser beam will not function efficiently in a water-vapor atmosphere. There is no mention of using water or air for cooling.

In *Plasti. Reconstr. Surg.* 6902::78 (1982) in an article titled "Chilling Port Wine Stains Improves The Response To Argon Laser Therapy" by B. A. Gilchrest, S. Rosen and J. M. Noe, the data obtained in this study suggests the potential benefit of port wine lesional modification by chilling the lesional sites by applying ice thereto for 2 to 3 minutes and then subjecting the sites to Argon laser therapy. It is further suggested that the benefit is due to reduced heat injury of nonvascular elements in the skin.

In *Plasti. Reconstr. Surg.* 75.1:42 (1985) in an article titled "The Benefit Of Chilling In Argon-Laser Treatment Of Port-Wine Stains" by B. Dreno, T. Patrice, P. Litoux and H. Barriere, the authors compare results obtained in Argon laser treatment of port-wine stains with and without preliminary chilling, noting that the success rate is considerably greater with the former procedure (68.6 percent) then with the latter (37.5 percent). The patients were classified as having good or unsatisfactory results four months after treatment. A good result corresponded to an evident blanching of the treated area, and an unsatisfactory result corresponded to slight or no blanching of the treated area. It should be noted that in the latter two studies, Argon laser treatment and cooling did not occur simultaneously.

SUMMARY OF THE INVENTION

Against the foregoing background, it is a primary object of the present invention to provide a substantially improved method for treating cutaneous vascular lesions, particularly lower extremity telangiectasia.

It is another important object of the present invention to provide substantially improved apparatus for treating cutaneous vascular lesions, particularly lower extremity telangiectasia.

It is still another important object of the present invention to provide such an improved method and apparatus for allowing for laser photo-coagulation and destruction of lower extremity telangiectasia while protecting the epidermal compartment from thermal injury that otherwise results from melanin absorption of laser light by cooling the epidermis and while simultaneously passing laser light through the cooled epidermis to the target vessels in the dermis.

It is yet another important object of the present invention to provide such an improved method and apparatus which minimizes injury to normal skin structures to reduce resulting pain and side effects of scabbing, scarring and/or hyperpigmentation.

It is a still further important object of the present invention to provide such an improved method and apparatus utilizing laser treatment and which avoids any refraction or other alteration of the physical characteristics of the laser light.

To the accomplishment of the foregoing objects and advantages, the method of the present invention, in brief summary, comprises the steps of delivering laser light to a desired target area of the skin of a patient while simultaneously delivering a transparent coolant to the epidermis at the location where it is entered by the laser beam.

The apparatus of the present invention, in brief summary, comprises a source of a laser beam, means for aiming the laser beam at a target area of a telangiectasia patient through the patient's epidermis, and means for delivering a transparent coolant to the patient's epidermis at the location where it is entered by the laser beam.

BRIEF DESCRIPTION OF THE DRAWINGS

The foregoing and still other objects and advantages of the present invention will be more apparent from the following detailed explanation of the preferred embodiments of the invention in connection with the accompanying drawings wherein.

DESCRIPTION OF THE PREFERRED EMBODIMENTS

Figure 1:
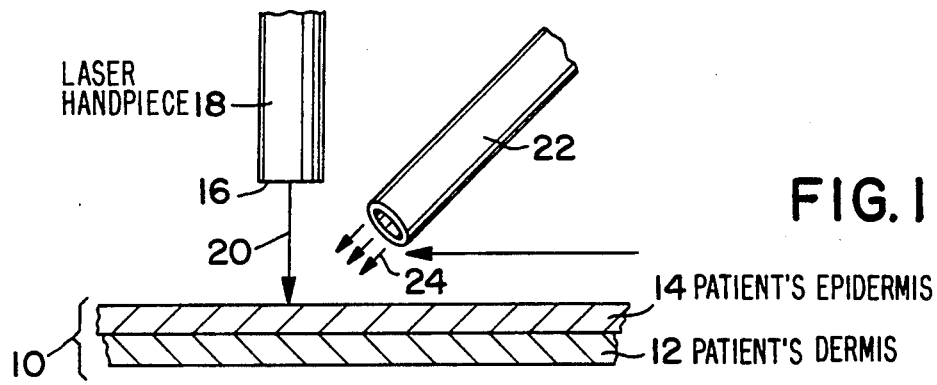
FIG. 1 is a somewhat schematic view showing a first preferred form of apparatus embodying the present invention being used to perform the method of the invention.

The purpose of this new laser surgery method and apparatus is to allow for laser photo-coagulation and destruction of lower extremity telangiectasia while protecting the epidermal compartment from thermal injury that otherwise results from melanin absorption of laser energy. Since laser light must pass through the melanin containing epidermis, on its way to the target vessels in the dermis, it is not possible to prevent some degree of heat generation when laser light hits melanin pigment. Indeed, yellow (tunable dye) laser light, although less efficiently absorbed by melanin than is blue-green (Argon) laser light, still causes significant hyperpigmentation as a long term side effect. In the invention, the epidermis is cooled simultaneously with the use of laser light. This cooling dissipates the heat generated by absorption of that light by melanin, thereby minimizing injury to normal skin structures to reduce resulting pain and side effects of scabbing, scarring and/or hyperpigmentation. Simultaneous cooling and lasing can be achieved in a number of ways.

FIGS. 1, 2, 3 and 4 show, somewhat schematically, first, second, third and fourth, respectively, preferred forms of apparatus for performing the method of the present invention. In each of these figures, the apparatus is illustrated in the course of treating telangiectasia, indicated as a lesion or target area 10 in a patient's dermis 12 which is overlaid by the patients's epidermis 14. It will be assumed without limitation that target vessels 10 are located in a lower extremity of the patient.

Each of FIGS. 1, 2, 3 and 4 depicts apparatus including a laser beam source 16 at the bottom end of a laser handpiece 18, a laser beam 20 being shown emanating from the beam source and impinging on a predetermined location of epidermis 14 substantially at right angles thereto and directly in line with target area 10 and on its way to the target area. The epidermis 14 contains melanin which would absorb laser energy, with resultant thermal injury, as discussed above.

Each apparatus shown in FIGS. 1, 2, 3 and 4 also includes means for subjecting the patients epidermis 14 to a cooling fluid at the predetermined location of the epidermis where laser beam 20 is to enter the epidermis simultaneous with the application of the laser beam thereto.

Specifically, in the apparatus of FIG. 1, the coolant is a transparent nonflammable gas 24 which is emitted from tube 22 at the treatment site simultaneous with the Argon laser treatment.

Figure 2:
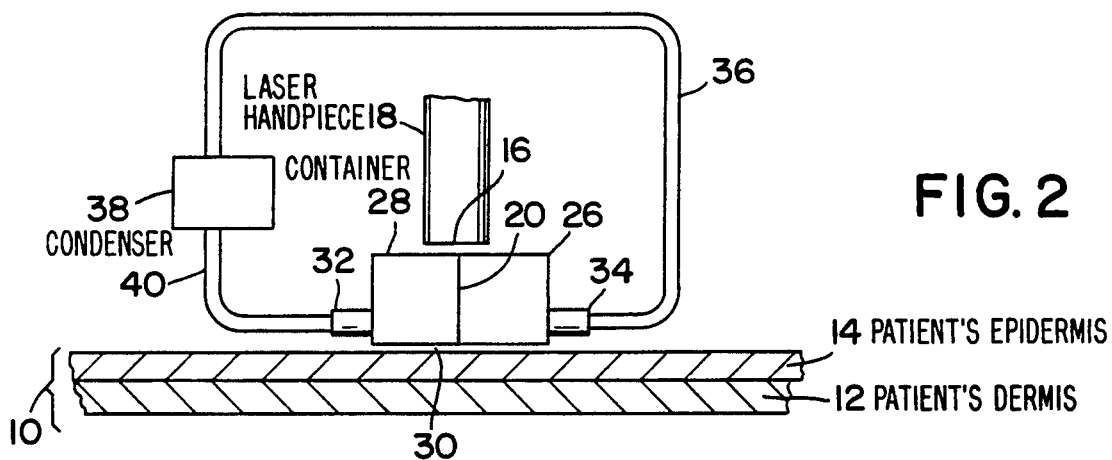
FIG. 2 is a view, similar to FIG. 1, showing a second preferred form of apparatus embodying the present invention being used to perform the method of the invention.

In the apparatus of FIG. 2, the cooling means is a cooling fluid provided in transparent container 26 having a pair of parallel opposite faces 28 and 30. The cooling fluid is applied at the treatment site simultaneous with the Argon laser treatment. The laser beam 20 is substantially perpendicular to the parallel opposite faces. Container 26 has an inlet tube 32 for inserting refrigerated cooling fluid into the container and an outlet tube 34 for removing heated fluid from the container to provide a stream of refrigerated cooling fluid in a direction parallel to and adjacent the outer surface of epidermis 14. Suitable piping 36 is provided to return the now heated fluid from outlet tube 34 through a condenser 38 to cool the fluid. Suitable piping 40 is also provided for returning fluid. (now again refrigerated) to inlet tube 32 and then once again into container 26.

Thus, the apparatus of FIG. 2 includes means for re-cooling heated fluid and thereafter re-introducing the re-cooled fluid into inlet tube 32.

Figure 3:
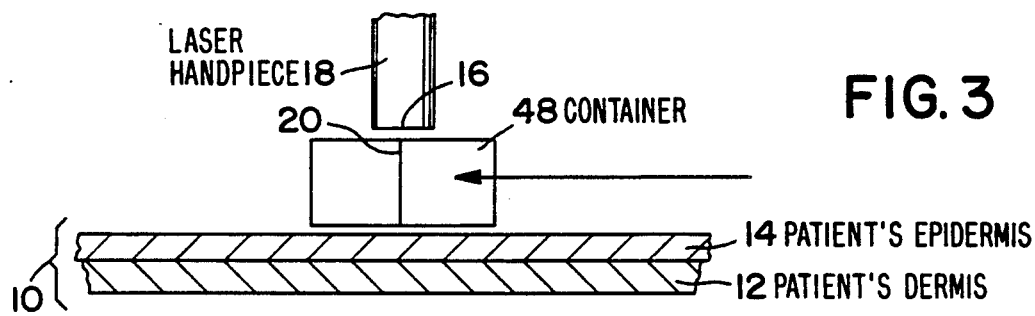
FIG. 3 is a view, similar to FIG. 1, showing a third preferred form of apparatus embodying the present invention being used to perform the method of the invention.
Figure 4:
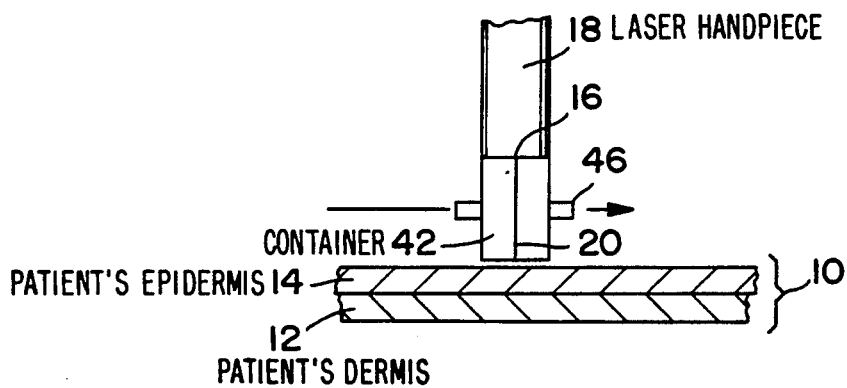
FIG. 4 is a view, similar to FIG. 1, showing a fourth preferred form of apparatus embodying the present invention being used to perform the method of the invention.

The apparatus of FIGS. 3 and 4 are similar to the apparatus of the FIG. 2 embodiment in that the coolant, preferably, is a liquid.

Specifically, the apparatus of FIG. 3 includes a transparent container 48 containing a cooling fluid which is a suitable liquid such as ice water. There are no inlet and outlet tubes. Accordingly, the ice water is substantially non-flowing. Container 48 is a first container and is replaceable by a second container (also 48) which contains more cooling fluid when the fluid or liquid in first container 48 becomes too warm for efficient use. First container 48 with its cooling liquid can then be cooled so as to be ready for reuse.

The apparatus of FIG. 4 is similar to the apparatus of FIG. 2 in that the FIG. 4 apparatus has a transparent container 42 with an inlet tube 44 and an outlet tube 46 for re-cycling cooling fluid, such as for example, non-flammable transparent liquid. Outlet tube 46 may be connected to a waste line (not shown) or connected back to inlet tube 44 via piping and a condenser as in the apparatus of FIG. 2. However, the apparatus of FIG. 4 differs from that of FIG. 2 in that container 42 is attached to laser handpiece 18 at laser beam source 16.

Figure 5:
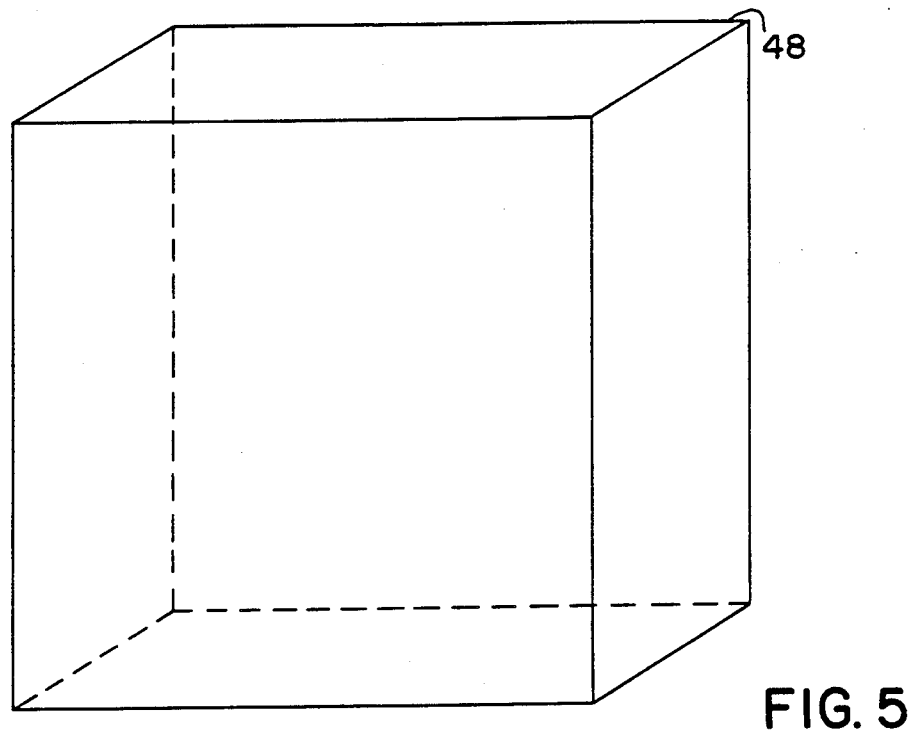
FIG. 5 is an enlarged perspective view showing a coolant container which is a component of the apparatus of FIG. 3.

FIG. 5 is an enlarged perspective view of container 48 of FIG. 3. As shown in FIG. 5, container 48 is a rectangular, parallel pipe structure which is about 6 inches (15.2 cm) by 6 inches (15.2 cm) by 2 inches (5.1 cm). Container 48 maybe fabricated of glass panels 0.125 inches (0.3 cm) thick.

Figure 6:
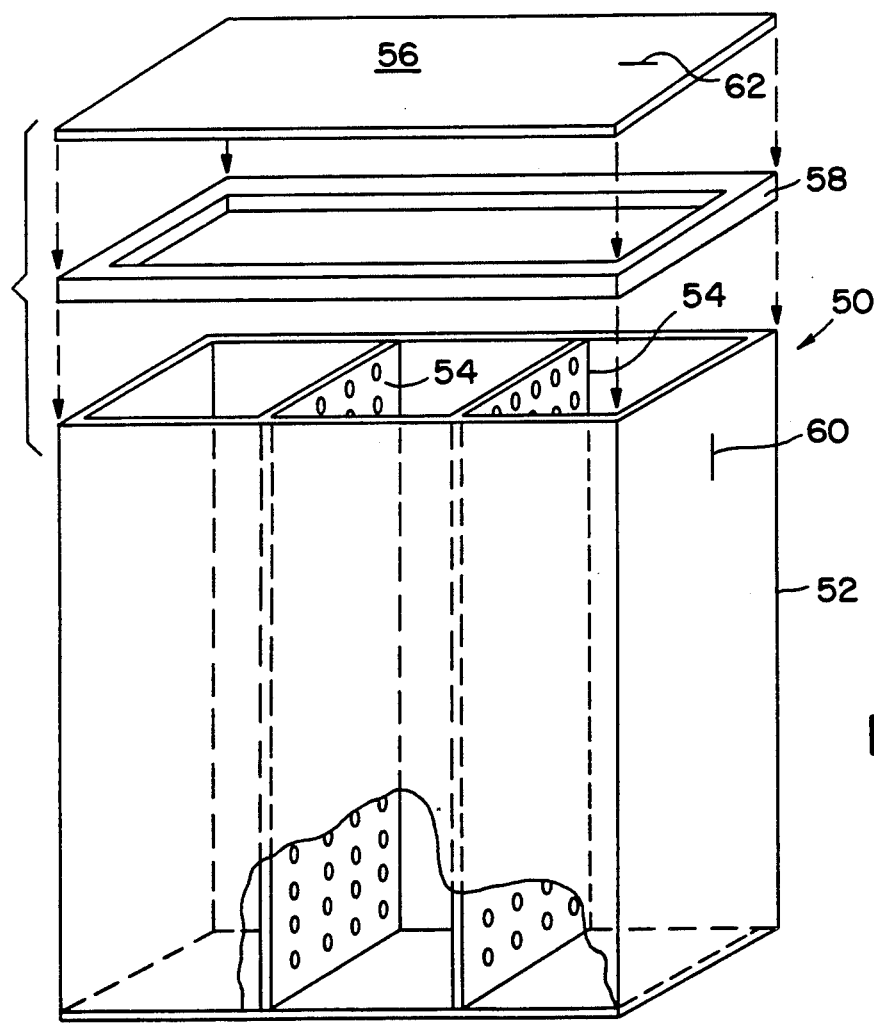
FIG. 6 is an enlarged perspective view similar to FIG. 5 but showing a modified form of a coolant container which may be used instead of the box of FIG. 5.

FIG. 6 is perspective view of a container 50 which is a modified form of a container (instead of container 48) for use in the apparatus of FIG. 3. Container 50 has a body 52 for containing the cooling fluid. Body 52 has perforated, spaced, parallel internal walls 54, a top 56 which covers body 52, and a sealing element 58 interposed between the body and the top. Sealing element 58 may be silicone. Body 52 is attached at 60 and top 56 is attached at 62.

Body 52 and top 56 may be fabricate of glass panels 0.125 inches (0.3 cm) thick. The dimension of body 52 may be about 6 inches (15.2 cm) wide by 1 inch (2.5 cm) deep by 7 inches (17.8 cm) high. Thus, top 56 is about 6 inches (15.2 cm) by 1 inch (2.5 cm).

The following is the result of the application of Argon laser treatment of lower extremity telangiectasia achieved with the simultaneous cooling of the treatment site. Specifically, pulses of two tenths of a second were applied onto three areas of a thigh of a subject. Each area was treated for approximately 15 minutes.

Results Of Argon Laser Treatment Of Lower Extremity Telangiectasia Achieved With Simultaneous Cooling Of The Treatment Site.

| SUBJECTIVE | | OBJECTIVE | | |
| --- | --- | --- | --- | --- |
| Pain of Treatment | Pain After Treatment | Immediate Response to Treatment (Nature of Wound) | Time To Full Healing | Result (1 month After Treatment) |
| Moderate and less painful than injection sclerotherapy | None | No scab Erythema and urtication of skin overlying treated vessels No echymosis or bleeding | 2-4 wks | Of the three sites which were fully treated: one is Excellent (98% gone) one is Good (70%-80% gone) one is Poor (20%-30% Gone) No scaring at any site |

Final result judged at four months—all three sites good to perfect. All three sites are without scarring, and treated vessels are gone or markedly reduced in appearance.

These results prove that the epidermis can be at least partly protected from thermal injury by virtue of simultaneous lasing and cooling. Without cooling, the same manner of laser usage routinely causes prominent scabs that persist for 3-6 weeks. Further, there are red to purple colored scars that require 4-12 months to fade. Simultaneous cooling has allowed for a virtual absence of scabbing and rapid resolution of the wound, without persistent marking or scaring.

It is like that the use of other kinds of lasers (tunable dye) with cooling will allow for more consistent results, with at least equally rapid healing and resolution, and less, if any, discomfort.

The having been thus described with particular reference to the preferred forms thereof, it will be obvious that various changes and modifications may be made therein without departing from the spirit and scope of the invention as defined in the appended claims.

Wherefore, I claim:

1. Apparatus for treating cutaneous vascular lesions in a target area under a patient's epidermis, said apparatus comprising:
   a laser beam source means for directing a laser beam against and through a predetermined location of the patient's epidermis to the target area; and
   a stationary container means for containing a cooling medium and for subjecting the patient's epidermis to the cooling medium at the target area of the patient's epidermis simultaneous with the application of the laser beam thereto, said container being a closed container and positioned directly between said laser beam source means and the target area of the patient's epidermis, but spaced from said laser beam source means.

2. Apparatus according to claim 1, wherein said container has a body for containing the cooling medium, said body having perforated spaced internal walls, a top for covering said body and a sealing element interposed between and sealed to said body and said top.

3. Apparatus for treating cutaneous vascular lesions in a target area under a patient's epidermis, said apparatus comprising:
   a laser beam source means for directing a laser beam against and through a predetermined location of the patient's epidermis to the target area;
   means for subjecting the patient's epidermis to a cooling medium at the predetermined location of the patient's epidermis simultaneous with the application of the laser beam thereto, said means being positioned between said laser beam source means and the target area; and
   closed recirculation means for inserting cooling fluid into said subjecting means and for removing heated cooling fluid from said subjecting means and for inserting re-cooled heated cooing fluid into said subjecting means, 4. Apparatus according to claim 3, wherein said means for subjecting the patient's epidermis to a cooling medium includes a transparent container having a pair of parallel opposite faces and containing a cooling fluid, said transparent container being positioned between said laser beam source and the predetermined location of the patient's epidermis with said pair of opposite faces substantially perpendicular to the laser beam.

5. Apparatus according to claim 3, wherein said means for subjecting the patient's epidermis to a cooling medium includes a transparent container for containing a cooling fluid positioned between said laser beam source and the predetermined location of the patient's epidermis, an inlet tube for inserting the cooling fluid into said container and an outlet tube for removing heated cooling fluid from said container, to provide a stream of refrigerated cooling fluid flowing in a direction parallel to and adjacent the surface of the patient's epidermis.

6. Apparatus according to claim 3, wherein said recirculation means is recirculating means for removing heated fluid, then re-cooling the heated fluid and thereafter re-introducing the re-cooled fluid into said subjecting means.

7. Apparatus according to claim 3, wherein said laser beam source means includes a laser handpiece.

8. Apparatus according to claim 5, wherein said laser beam source means includes a laser handpiece having an end and said transparent container is attached to said handpiece at said end thereof.

9. Apparatus according to claim 4, wherein said container is a first container and said fluid is a substantially non-flowing liquid in said first container, and wherein said first container is replaceable with a second container which is similar to said first container when the temperature of said fluid in said first container has risen to a predetermined temperature.

10. Apparatus according to claim 9, wherein said first and said second containers each is a rectangular, parallel piped structure.

11. Apparatus according to claim 10, wherein said first and said second containers each has a body containing said fluid and having perforated spaced internal walls, a top for covering said body and a sealing element interposed between and sealed to said body and said top.

* * * * *

UNITED STATES PATENT AND TRADEMARK OFFICE
CERTIFICATE OF CORRECTION

PATENT NO. : 5,057,104
DATED : October 15, 1991
INVENTOR(S) : Cyrus Chess

It is certified that error appears in the above-identified patent and that said Letters Patent is hereby corrected as shown below:

<u>IN THE DRAWINGS</u>

In Fig. 4, please add the reference numeral 44.

Col. 2, line 34, change "6902::78 (1982)" to --69.2:278 (1982)--.

Col. 6, line 12, change "like" to --likely--;

line 16, after "The" insert --invention--;

Col. 6, line 58, (claim 3, line 16), change "cooing" to --cooling--.

Signed and Sealed this

Eighth Day of March, 1994

Attest:

BRUCE LEHMAN

*Attesting Officer*  *Commissioner of Patents and Trademarks*